(12) United States Patent
Xu et al.

(10) Patent No.: US 10,993,955 B2
(45) Date of Patent: *May 4, 2021

(54) MEDICAMENT FOR USE IN TREATING DIABETES

(71) Applicant: Shandong Zhonghai Pharmaceutical CO. LTD, Weifang (CN)

(72) Inventors: Baozhen Xu, Weifang (CN); Qian Cheng, Weifang (CN); Long Cheng, Weifang (CN)

(73) Assignee: SHANDONG ZHONGHAI PHARMACEUTICAL CO. LTD, Weifang (CN)

( * ) Notice: Subject to any disclaimer, the term of this patent is extended or adjusted under 35 U.S.C. 154(b) by 249 days.

This patent is subject to a terminal disclaimer.

(21) Appl. No.: 16/073,848

(22) PCT Filed: Jan. 20, 2017

(86) PCT No.: PCT/CN2017/071858
§ 371 (c)(1),
(2) Date: Jul. 30, 2018

(87) PCT Pub. No.: WO2017/129057
PCT Pub. Date: Aug. 3, 2017

(65) Prior Publication Data
US 2019/0038649 A1     Feb. 7, 2019

(30) Foreign Application Priority Data

Jan. 29, 2016 (CN) .......................... 201610061749.6

(51) Int. Cl.
| | | |
|---|---|---|
| A61K 38/16 | (2006.01) | |
| A61K 31/7012 | (2006.01) | |
| A61K 36/315 | (2006.01) | |
| A61K 36/03 | (2006.01) | |
| A61K 36/488 | (2006.01) | |
| A61K 36/04 | (2006.01) | |
| A61K 36/05 | (2006.01) | |
| A61P 3/10 | (2006.01) | |
| A61K 31/404 | (2006.01) | |
| A61K 36/28 | (2006.01) | |
| A61K 36/48 | (2006.01) | |
| A61K 36/9064 | (2006.01) | |

(52) U.S. Cl.
CPC ........ *A61K 31/7012* (2013.01); *A61K 31/404* (2013.01); *A61K 36/03* (2013.01); *A61K 36/04* (2013.01); *A61K 36/05* (2013.01); *A61K 36/28* (2013.01); *A61K 36/315* (2013.01); *A61K 36/48* (2013.01); *A61K 36/488* (2013.01); *A61K 36/9064* (2013.01); *A61K 38/168* (2013.01); *A61P 3/10* (2018.01)

(58) Field of Classification Search
CPC .................................................. A61K 38/168
See application file for complete search history.

(56) References Cited

FOREIGN PATENT DOCUMENTS

| | | | |
|---|---|---|---|
| CN | 101760492 | A | 6/2010 |
| CN | 105535927 | A | 5/2016 |
| CN | 105535954 | A | 5/2016 |
| CN | 105582522 | A | 5/2016 |
| CN | 105597080 | A | 5/2016 |
| CN | 105597081 | A | 5/2016 |
| CN | 105617354 | A | 6/2016 |
| CN | 105617355 | A | 6/2016 |
| CN | 105617356 | A | 6/2016 |
| CN | 105641681 | A | 6/2016 |
| CN | 105709206 | A | 6/2016 |
| CN | 105709207 | A | 6/2016 |
| ES | 2232273 | A1 | 5/2005 |
| JP | 60255722 | A | 11/1985 |
| WO | 2005117937 | A2 | 12/2005 |

OTHER PUBLICATIONS

Domozych et al., "The comparative aspects of cell wall chemistry in the green algae (*Chlorophyta*)," J Mol Evol 15:1-12, 1980.*
Kim et al., "Hypoglycemic effect of *Chlorella* sp. CMS-1 hot water extract on streptozoticin-induced diabetic rats," J Life Sci 18(11):1584-1591, 2008.*
English machine translation of Wang (CN 101564138 A), 2009.*
English machine translation of Dimarchi et al., CN 104114183 A, 2014.*
Go,H. et al.,"A Glycoprotein from Laminaria Japonica Induces Apoptosis in HT-29 Colon Cancer Cells", Toxicology In Vitro, vol. 24, No. 6, Jul. 6, 2010 (Jul. 6, 2010), abstract.

* cited by examiner

*Primary Examiner* — Rosanne Kosson
(74) *Attorney, Agent, or Firm* — Bayramoglu Law Offices LLC

(57) ABSTRACT

A medicament for treating diabetes and complications thereof, the medicament being a glycoprotein, or a mixture of a polysaccharide and a protein, or a polypeptide, or a protein.

10 Claims, No Drawings

MEDICAMENT FOR USE IN TREATING DIABETES

CROSS REFERENCE TO RELATED APPLICATIONS

This application is the national phase entry of International Application No. PCT/CN2017/071858, filed on Jan. 20, 2017, which is based upon and claims priority to Chinese Patent Application No. 201610061749.6, filed on Jan. 29, 2016, the entire contents of which are incorporated herein by reference.

TECHNICAL FIELD

The present invention relates to a medicament for use in treating diabetes, and belongs to the field of medical technology.

BACKGROUND

Diabetes is a chronic metabolic disease characterized by hyperglycemia, which is caused by impairment in insulin secretion or its biological effects, or both. Diabetes can't be radically cured and is accompanied by several other diseases. It remains the leading cause of blindness among the people aged 25-74. 10% of diabetic patients are complicated by kidney disease. Diabetes is the commonest cause of non-traumatic lower extremity resection and diabetic patients has a risk for leg resection increased by 30 times, a risk of developing heart disease increased by 2-4 times, and a likelihood of developing stroke increased by 5 times.

The etiology of diabetes remains unclear, and both genetic and environmental factors appear to play a part. Diabetes has two categories: insulin dependent (type I) and non-insulin dependent (type II).

Type I diabetes is an autoimmune disease that often occurs in children and young adults. The autoantigen that causes type 1 diabetes still remains unknown, and the patient's survival depends on daily intravenous injection of insulin.

Type II diabetes is considered to be a metabolic disease because the body cannot produce a sufficient amount of insulin or the insulin, though generated, cannot be properly used; it is considered to be the commonest type of diabetes. Although it is known that lack of insulin secretion and resistance to insulin are the main causes of type 2 diabetes, the precise genetic factors still remain unclear. Diabetic patients usually have one or more of the following defects. They are: excessively low insulin produced by the pancreas; excessive glucose secreted by the liver; skeletal muscular dysfunction in using glucose; glucose transporter (Glut-1, Glut-2) dysfunction; insulin receptor desensitization and polysaccharide metabolic and decomposition dysfunction.

Patent: Use of soluble myeloid cell-surface glycoprotein in the treatment or prevention of chronic inflammatory conditions and clinical disorders of insulin resistance e.g. type 2 diabetes and obesity, Patent No. ES2232273 (A1), it is disclosed that: soluble myeloid surface glycoprotein (soluble CD14 (sCD14) for the treatment or prevention of animal or human-associated clinical chronic inflammatory conditions, with anti-inflammatory, anti-diabetic, anti-arteriosclerotic, anti-hypertensive and hypolipidemic effects; it can reduce the level of mouse's serum glucose and serum insulin concentration.

Patent ALPHA-1-ACID GLYCOPROTEIN FOR THE TREATMENT OF DIABETES, Patent No. WO2005117937 (A2) it is disclosed that: "a method using α-1-acid glycoprotein, or its active derivative, to regulate the level of glucose in blood in mammals, especially humans; alpha-1-acid glycoprotein administered to patients with type 1 or type 2 diabetes can lower blood glucose levels. The present invention provides the application of an α-1-acid glycoprotein or its reactive derivative for the preparation of a medicament for treating diabetes, which is used to reduce the blood glucose level of patients with acute-phase proteins, or the application of a medicament for treating chronic or subchronic inflammation.

Patent: AMINO ACID TRANSFUSION FOR DIABETES, Patent No. JPS60255722 (A), discloses: an amino acid infusion containing free amino acids, equivalent to 47-53 wt % of total amino acids, including L-leucine, L-proline, L-alanine, L-arginine, the above-mentioned amino acid infusion solution has an effect of promoting insulin secretion, and can reduce the dose of the used insulin medicaments.

The present diabetes treatment medicaments have the following defects:

(1) The blood glucose lowering effect is not obvious;

(2) The reduction of blood glucose and urine glucose is small, and the needs of diabetic patients in all age groups cannot be satisfied simultaneously;

(3) After the medicament withdrawal, the blood glucose and urine glucose concentration fluctuate greatly.

SUMMARY

The present invention provides a medicament for use in treating diabetes in order to solve the deficiencies in the prior art for the purpose to achieve the following objectives hereof:

(1) The medicament hereof has a significant effect on lowering blood glucose in rat models of diabetes;

(2) The medicament hereof has a significant effect on lowering blood and urine glucose in diabetic patients at different age groups;

(3) The medicament hereof has a small fluctuation in blood glucose and urine glucose after being withdrawn for 2 months; for patients aged from 16 to 45 years old, the blood glucose concentration rises by 2-3%, and the urine glucose is ≤1.0 mmol/L; for patients aged from 46 to 75 years old, the blood glucose concentration rises by 3-5%, and the urine glucose concentration rises by 7-9%.

In order to solve the aforesaid problems, the present invention adopts the following technical solution:

A medicament for use in treating diabetes, characterized in that the medicament is a glycoprotein or a mixture polysaccharide and protein or a polypeptide or a protein; the said glycoprotein comprises, by weight content, 1-99% sugar and 1-99% protein; the mixture of polysaccharide and protein, by weight content, comprises 1-99% sugar and 1-99% protein. The molecular weight of the glycoprotein is 0.2 to 3000 kDa;

The following are further modifications to the above technical solution:

The medicament is a marine algal glycoprotein.

The said marine algal glycoprotein comprises, by weight content, 1-99% sugar and protein ( ); the said mixture of marine algal polysaccharide and protein, by weight content, comprises 1-99% sugar and 1-99% protein.

The said marine algal glycoprotein has a molecular weight of 0.2-3000 kDa;

As for the said mixture of polysaccharide and the protein, the polysaccharide has a molecular weight of 0.2-3000 kDa and the protein has a molecular weight of 0.2-3000 kDa.

The said medicament comprises, by weight content, 1-99 portions of glycoprotein and 1-25 portions of glucuronic acid.

The said medicament comprises, by weight content, 1-99 portions of marine algal glycoprotein and 1-24 portions of glucuronic acid.

The said medicament comprises, by weight content, 1-99 portions of marine algal glycoprotein, 1-20 portions of glucuronic acid and 3-10 portions of natural indigo.

The said alga is one kind among the following: blue alga, green alga, red alge, golden alga, and brown alga.

The said medicament comprises, by weight content, 1-99 portions of marine algal glycoprotein, 6-14 portions of natural indigo, and 7-15 portions of amomum cardamomum and 1-16 portions of glucuronic acid.

The said medicament comprises, by weight content, 1-99 portions of marine algal glycoproteins, 6-14 portions of indigo naturalis, 7-15 portions of amomum cardamomum, 8-12 portions of Chrysanthemum, and 8-10 portions of radix puerariae.

The said medicament comprises, by weight content, 1-99% sugar and 1-99% protein.

The said marine algal glycoprotein comprises, by weight content, 1-99% sugar and 1-99% protein.

Compared with the prior art, the advantages of the present invention are:

(1) The medicament hereof has a significant effect on lowering blood glucose in a rat model of diabetes. At 4 weeks after the initiation of the administration, the blood glucose of the rats decreases from 27.06-27.19 mmol/L to 11.26-23.41 mmol/L; the blood glucose of the rats in the model control group increase from 27.15 mmol/L to 39.87 mmol/L.

(2) The medicament hereof has a significant effect on reducing blood glucose and urine glucose in diabetic patients. After 3-month treatment, for patients aged 16-30 years old, the blood glucose concentration is 6.0 mmol/L, and the urine glucose concentration is 0.7 mmol/L; as for patients aged 31-45 years old, the blood glucose concentration is 6.4-6.6 mmol/L, and the urine glucose concentration is 22.0-22.7 mmol/L; for patients aged 46-60 years old, the blood glucose concentration is 6.8-7.0 mmol/L, and the urine glucose concentration is 15.0-15.8 mmol/L; for patients aged 61-75 years, the blood glucose concentration is 8.5-8.8 mmol/L, and the urine glucose concentration is 15-18 mmol/L.

(3) The medicament hereof has a small fluctuation in blood glucose and urine glucose after being withdrawn for 2 months; for patients aged from 16 to 45 years old, the blood glucose concentration rises only by 2-3%, and the urine glucose is ≤1.0 mmol/L; for patients aged from 46 to 75 years old, the blood glucose concentration rises by 3-5%, and the urine glucose concentration rises by 7-9%.

DETAILED DESCRIPTION OF THE EMBODIMENTS

The preferred embodiments of the present invention are described in the following, and the preferred embodiments described herein are only intended to illustrate and explain the invention, but not limited to this invention.

Embodiment 1 A Medicament for Use in Treating Diabetes

The said medicament is a marine algal glycoprotein;
The said marine algal glycoprotein comprises, by weight content, 1% sugar and 99% protein.
The molecular weight is 0.2 kDa;
The said marine algae is blue algae;
The said sugar is a polysaccharide;
The said polysaccharide comprises: glucose, mannose, rhamnose, galactose;
The said protein comprises: aspartic acid, glutamic acid, glycine, arginine, lysine, serine, and threonine.

Embodiment 2 A Medicament for Use in Treating Diabetes

The said medicament is a marine algal glycoprotein;
The said marine algal glycoprotein comprises, by weight content, 8% sugar and 80% protein.
The molecular weight is 10 kDa;
The said marine algae is green algae;
The said sugar is a polysaccharide;
The said polysaccharide comprises: glucose, mannose, rhamnose, galactose;
The said protein comprises: aspartic acid, glutamic acid, glycine, arginine, lysine, serine, and threonine.

Embodiment 3 A Medicament for Use in Treating Diabetes

The said medicament is a marine algal glycoprotein;
The said marine algal glycoprotein comprises, by weight content, 15% sugar and 70% protein.
The molecular weight is 5 kDa;
The said marine algae is blue algae;
The said sugar is a polysaccharide;
The said polysaccharide comprises: glucose, mannose, rhamnose, galactose;
The said protein comprises: aspartic acid, glutamic acid, glycine, arginine, lysine, serine, and threonine.

Embodiment 4 A Medicament for Use in Treating Diabetes

The said medicament is a marine algal glycoprotein;
The said marine algal glycoprotein comprises, by weight content, 30% sugar and 50% protein.
The molecular weight is 150 kDa;
The marine algae is red algae;
The said sugar is a polysaccharide;
The said polysaccharide comprises: glucose, mannose, rhamnose, galactose;
The said protein comprises: aspartic acid, glutamic acid, glycine, arginine, lysine, serine, and threonine.

Embodiment 5 A Medicament for Use in Treating Diabetes

The said medicament is a marine algal glycoprotein;
The said marine algal glycoprotein comprises, by weight content, 50% sugar and 20% protein.
The molecular weight is 800 kDa;
The said marine algae is brown algae;
The said sugar is a polysaccharide;
The said polysaccharide comprises: glucose, mannose, rhamnose, galactose;

The said protein comprises: aspartic acid, glutamic acid, glycine, arginine, lysine, serine, and threonine.

Embodiment 6 A Medicament for Use in Treating Diabetes

The said medicament is a marine algal glycoprotein;
The said marine algal glycoprotein comprises, by weight content, 99% sugar and 1% protein.
The molecular weight is 3000 kDa;
The said marine algae is gold algae;
The said sugar is a polysaccharide;
The said polysaccharide comprises: glucose, mannose, rhamnose, galactose;
The said protein comprises: aspartic acid, glutamic acid, glycine, arginine, lysine, serine, and threonine.
The glycoprotein said in these above embodiments 1-6 further includes a pigment; the said pigment is a natural pigment contained in algal substances;
These above embodiments 1-6 could be summarized as:
A Medicament for Use in Treating Diabetes
The said medicament is a glycoprotein;
The said glycoprotein comprises, by weight content, 1-99% sugar and 1-99% protein;
The molecular weight is 0.2-30000 kDa;
The said sugar is a polysaccharide;
The said medicament includes synthetic glycoproteins and synthetic polysaccharides and proteins.
The said protein comprises 20 kinds of amino acids and 8 kinds of synthetic amino acids; The preparation method of the said medicament: the glycoprotein is prepared into capsules and tablets etc. according to a conventional process; the mixture of the polysaccharide and the protein is prepared into capsules and tablets etc. according to a conventional process.

Embodiment 7 A Medicament for Use in Treating Diabetes

The test on the effect of the medicament hereof on blood glucose of a rat model of streptozotocin-induced diabetes is shown in Table 1-2.

Animal: SD rats, male, 200-230 g, SPF grade, license number: SCXK (Beijing) 2006-0009;
Breeding environment: Experimental Animal Center of CACMS (in the barrier environment), license number: SYXK (Beijing) 2005-0028;
Streptozotocin: (STZ), US Signa product, batch number: 038k1523
SD rats are taken for adaptive feeding for 2 days, 11 rats are randomly selected and divided into the normal control group, and the remaining rats are divided into the experimental groups and evenly grouped according to body weight, with 17 rats in each group. After fasting for 12 hours, the animals in the experimental groups are intraperitoneally injected with STZ 60 mg/Kg, 0.6 ml/100 Kg body weight (dissolved in 0.1 mmol·L−1 citrate buffer with a pH of 4.5), and the rats in the control group was injected with citrate buffer of an equal volume. 7 days after the injection in the control group and the experimental groups, blood was collected from animal's orbit and the blood glucose level after 12-hour fasting was measured by glucose oxidase method. A blood glucose concentration of more than 10.05 mmol·L−1 is a criterion for a qualified animal model of diabetes.

The qualified rat models are randomly divided into 8 groups, namely, a model control group, a test group of the present invention 1 g/day, a test group of the present invention 2 g/day, a test group of the present invention 3 g/day, and a test group of the present invention 4 g/day, a test group of the present invention 6 g/day, the test group of the present invention 8 g/day, and the blank control group, with 13-14 per group. The rats in the experimental group are intragastrically administered 3 times a day, and those in the control group were given distilled water of the same volume for 4 weeks. During the administration, the rats in the control group and the test group are administered normal feed, they can drink normally, without restrictions in feeds and water drinking.

TABLE 1

The effect of the medicament hereof at different doses on blood glucose of a rat model of streptozotocin-induced diabetes

| Group | Dose (g/day) | Blood glucose before administration (mmol/L) | Blood glucose after administration at different times (mmol/L) | | | |
|---|---|---|---|---|---|---|
| | | | One Week | Two Weeks | Three Weeks | Four Weeks |
| No-treatment Control Group | — | 4.45 ± 0.71 | 4.33 ± 0.79 | 4.40 ± 0.63 | 5.30 ± 0.73 | 6.55 ± 0.68 |
| Model control group | — | 22.15 ± 6.09 | 22.33 ± 5.51 | 27.51 ± 6.27 | 31.79 ± 7.12 | 36.87 ± 5.96 |
| Embodiment 2 | 1 | 21.99 ± 6.78 | 29.17 ± 5.95 | 27.59 ± 6.10 | 32.47 ± 3.45 | 47.17 ± 8.19 |
| Embodiment 2 | 2 | 22.06 ± 5.51 | 23.23 ± 7.02 | 24.82 ± 7.89 | 27.79 ± 8.51 | 35.46 ± 11.86 |
| Embodiment 2 | 3 | 22.02 ± 5.31 | 21.23 ± 7.14 | 19.82 ± 7.39 | 17.79 ± 8.12 | 15.46 ± 10.12 |
| Embodiment 2 | 4 | 27.19 ± 5.82 | 19.28 ± 5.74 | 17.45 ± 7.25 | 15.45 ± 5.74 | 12.26 ± 8.71 |
| Embodiment 2 | 6 | 22.11 ± 5.11 | 21.43 ± 6.56 | 19.08 ± 7.41 | 16.99 ± 8.29 | 13.76 ± 10.78 |
| Embodiment 2 | 8 | 21.86 ± 5.52 | 20.23 ± 6.12 | 19.82 ± 6.89 | 17.79 ± 7.30 | 16.26 ± 6.45 |

As can be seen from the above table, the medicament at the 3-8 g/day dose has a significant effect on lowering the blood glucose of the rat model of streptozotocin-induced diabetes, preferably at the dose of 4-6 g/day.

TABLE 2

The effect of the different types of medicaments hereof on blood glucose of a rat model of streptozotocin-induced diabetes

| Group | Dose (g/day) | Blood glucose before administration (mmol/L) | Blood glucose after administration at different times (mmol/L) | | | |
|---|---|---|---|---|---|---|
| | | | One Week | Two Weeks | Three Weeks | Four Weeks |
| Normal control group | — | 4.45 ± 0.71 | 4.33 ± 0.79 | 4.40 ± 0.63 | 5.30 ± 0.73 | 6.55 ± 0.68 |
| Model control group | — | 27.15 ± 6.09 | 29.33 ± 5.51 | 33.51 ± 6.27 | 35.79 ± 7.12 | 39.87 ± 5.96 |
| Embodiment 1 | 4 | 27.08 ± 5.95 | 19.53 ± 5.92 | 17.12 ± 7.49 | 14.01 ± 5.83 | 12.80 ± 9.13 |
| Embodiment 2 | 4 | 27.19 ± 5.82 | 19.28 ± 5.74 | 17.45 ± 7.25 | 15.45 ± 5.74 | 12.26 ± 8.71 |
| Embodiment 3 | 4 | 27.13 ± 5.72 | 18.28 ± 5.74 | 17.05 ± 7.05 | 12.35 ± 5.64 | 11.26 ± 7.71 |
| Embodiment 4 | 4 | 27.06 ± 5.91 | 20.03 ± 5.55 | 20.47 ± 5.98 | 18.65 ± 6.37 | 15.20 ± 5.34 |
| Embodiment 5 | 4 | 27.06 ± 5.91 | 22.03 ± 5.61 | 21.47 ± 5.98 | 19.15 ± 5.47 | 16.20 ± 5.34 |
| Embodiment 6 | 4 | 27.12 ± 6.35 | 23.31 ± 5.45 | 22.22 ± 6.12 | 20.34 ± 6.45 | 23.41 ± 5.46 |

From the results of Table 2, it can be seen that the medicaments in Embodiments 1-6 have a effect on reducing the blood glucose of the rat models of streptozotocin-induced diabetes, and Embodiments 2-3 are preferred embodiments.

Embodiment 8 A Medicament for Use in Treating Diabetes

The medicament hereof is used to compare the therapeutic effects in diabetic patients, and the details are as follows:

The applicant has divided 100 diabetic patients into treatment group. Among these patients, 6 are aged 16 to 30 years old, 14 are 31 to 45 years old, 28 are 46 to 60 years old, and 52 are 61 to 75 years old. Examination results show that, their fasting blood glucose is above 10.5 mmol/L, urine glucose is 65~117.1 mmol/L, and 100 patients with the age, medical history, and conditions similar to those in the treatment group are divided into the control group to demonstrate the efficacy of the medicament hereof.

During the treatment, the patients in the treatment group discontinue the administration of any other medicaments, and only take the medicament described in Embodiment 3 hereof, once in the morning and evening, 2 g each time; the patients in the control group take D-860 Rastinon according to the package insert, and the patients in treatment group and the control group of the invention were treated and observed for 3 months, and the results are as follows:

TABLE 3

| | Control group | | Treatment group | |
|---|---|---|---|---|
| | Blood sugar mmol/L | Glucose in urine mmol/L | Blood sugar mmol/L | Glucose in urine mmol/L |
| 16-30 | 6.2 | 1.0 | 6.0 | 0.7 |
| 31-45 | 6.5-6.7 | 28.6-32.2 | 6.4-6.6 | 22.0-22.7 |
| 46-60 | 7.3-7.6 | 31-35 | 6.8-7.0 | 15.0-15.8 |
| 61-75 | 9.0-9.2 | 35-58 | 8.5-8.8 | 15-18 |

The medicament hereof has no adverse effect, and has a small fluctuation in blood glucose and urine glucose after being withdrawn for 2 months; for patients aged from 16 to 45 years old, the blood glucose concentration rises only by 2-3%, and the urine glucose is ≤1.0 mmol/L; for patients aged from 46 to 75 years old, the blood glucose concentration rises by 3-5%, and the urine glucose concentration rises by 7-9%.

Embodiment 9 A Medicament for Use in Treating Diabetes

Calculated in content by weight, said medicament includes 1 marine algal glycoprotein and 1 glucuronic acid.

The said marine algal glycoprotein comprises, by weight content, 8% sugar and 80% protein.

The molecular weight is 15 kDa;

The said marine algal glycoproteins is the chlorella;

The said sugar is a polysaccharide;

The said polysaccharide comprises: glucose, mannose, rhamnose, galactose;

The said protein comprises: aspartic acid, glutamic acid, glycine, arginine, lysine, serine, and threonine.

Embodiment 10 A Medicament for Use in Treating Diabetes

Like Embodiment 9, only the ratio of marine algal glycoprotein to glucuronic acid is changed as follows:

The said medicament includes 32 marine algal glycoprotein and 7 glucuronic acid.

Embodiment 11 A Medicament for Use in Treating Diabetes

Like Embodiment 9, only the ratio of marine algal glycoprotein to glucuronic acid is changed as follows:

The said medicament includes 62 marine algal glycoprotein and 17 glucuronic acid.

Embodiment 12 A Medicament for Use in Treating Diabetes

Like Embodiment 9, only the ratio of marine algal glycoprotein to glucuronic acid is changed as follows:

The said medicament includes 99 marine algal glycoprotein and 24 glucuronic acid.

Embodiment 13 A Medicament for Use in Treating Diabetes

It comprises, by weight content, the following components:

1 portion of marine algal glycoprotein, 1 portion of glucuronic acid, and 3 portions of natural indigo.

The said marine algal glycoprotein comprises, by weight content, 15% sugar and 70% protein.

The molecular weight is 8 kDa;
The said marine alga is blue alga;
The said sugar is a polysaccharide;
The said polysaccharide comprises: glucose, mannose, rhamnose, galactose;
The said protein comprises: aspartic acid, glutamic acid, glycine, arginine, lysine, serine, and threonine.

Embodiment 14 A Medicament for Use in Treating Diabetes

Like Embodiment 13, only the ratio of marine algal glycoprotein, glucuronic acid and natural indigo is changed as follows:

It comprises, by weight content, the following components:

31 portions of marine algal glycoprotein, 7 portions of glucuronic acid and 5 portions of natural indigo.

Embodiment 15 A Medicament for Use in Treating Diabetes

Like Embodiment 13, only the ratio of marine algal glycoprotein, glucuronic acid and natural indigo is changed as follows:

It comprises, by weight content, the following components:

57 portions of marine algal glycoprotein, 15 portions of glucuronic acid and 8 portions of natural indigo.

Embodiment 16 A Medicament for Use in Treating Diabetes

Like Embodiment 13, only the ratio of marine algal glycoprotein, glucuronic acid and natural indigo is changed as follows:

It comprises, by weight content, the following components:

99 portions of marine algal glycoprotein, 20 portions of glucuronic acid and 10 portions of natural indigo.

Application of the Said Medicament in Embodiment 9-Embodiment 16 in Treating Diabetes Applying the test method mentioned in Embodiment 7 and Embodiment 8, and medicament mentioned in Embodiment 9-16, the applicable effects are as follows:

TABLE 4

The effect of the medicament hereof on blood glucose of a rat model of streptozotocin-induced diabetes

| Group | Dose (g/day) | Blood glucose before administration (mmol/L) | Blood glucose after administration at different times (mmol/L) | | | |
|---|---|---|---|---|---|---|
| | | | One Week | Two Weeks | Three Weeks | Four Weeks |
| Normal control group | — | 4.45 ± 0.71 | 4.33 ± 0.79 | 4.40 ± 0.63 | 5.30 ± 0.73 | 6.55 ± 0.68 |
| Model control group | — | 27.15 ± 6.09 | 29.33 ± 5.51 | 33.51 ± 6.27 | 35.79 ± 7.12 | 39.87 ± 5.96 |
| Embodiment 9 | 4 | 27.08 ± 5.95 | 19.23 ± 5.92 | 17.32 ± 7.49 | 15.01 ± 5.83 | 12.30 ± 9.13 |
| Embodiment 10 | 4 | 27.19 ± 5.82 | 19.28 ± 5.74 | 17.45 ± 7.25 | 15.45 ± 5.80 | 12.26 ± 8.71 |
| Embodiment 11 | 4 | 27.13 ± 5.72 | 16.35 ± 5.53 | 15.78 ± 7.58 | 12.36 ± 5.57 | 9.24 ± 8.60 |
| Embodiment 12 | 4 | 27.06 ± 5.91 | 19.28 ± 5.74 | 17.45 ± 7.05 | 15.45 ± 5.64 | 12.26 ± 8.70 |
| Embodiment 13 | 4 | 27.06 ± 5.91 | 19.28 ± 5.74 | 17.45 ± 7.37 | 15.45 ± 5.90 | 12.26 ± 8.61 |
| Embodiment 14 | 4 | 27.12 ± 6.35 | 19.28 ± 5.74 | 17.45 ± 7.45 | 15.45 ± 5.84 | 12.26 ± 8.51 |
| Embodiment 15 | 4 | 27.15 ± 6.25 | 16.54 ± 5.69 | 15.64 ± 7.20 | 12.45 ± 5.67 | 9.08 ± 8.90 |
| Embodiment 16 | 4 | 27.18 ± 6.08 | 19.28 ± 5.74 | 17.45 ± 7.61 | 15.45 ± 5.74 | 12.26 ± 8.54 |

TABLE 5

The effect of the medicament hereof on urine glucose

| | Embodiment 9 | Embodiment 10 | Embodiment 11 | Embodiment 12 | Embodiment 13 | Embodiment 14 | Embodiment 15 | Embodiment 16 |
|---|---|---|---|---|---|---|---|---|
| | Glucose in urine mmol/L | | | | | | | |
| 16-30 | 0.6 | 0.57 | 0.25 | 0.6 | 0.57 | 0.55 | 0.22 | 0.61 |
| 31-45 | 22.5 | 22.1 | 17.5 | 22.4 | 22.0 | 21.8 | 17.0 | 21.6 |
| 46-60 | 14.8 | 14.2 | 10.9 | 14.6 | 14.0 | 14.2 | 10.2 | 14.5 |
| 61-75 | 14.7 | 14.3 | 9.7 | 14.5 | 14.9 | 14.8 | 9.5 | 15.0 |

The medicament hereof has no adverse effect, and has a small fluctuation in blood glucose and urine glucose after being withdrawn for 2 months; for patients aged from 16 to 45 years old, the blood glucose concentration rises only by 2.5%, and the urine glucose is ≤0.8 mmol/L; for patients aged from 46 to 75 years old, the blood glucose concentration rises by 2.7%, and the urine glucose concentration rises by 6.7%.

TABLE 6

Effect of the medicament hereof on the immune organs of rat model induced by streptozotocin-induced diabetes

| Group | Dose (g/day) | Thymus (g/100 g Weight) | Spleen (g/100 g Weight) |
|---|---|---|---|
| Normal control group | | 0.092 ± 0.016 | 0.204 ± 0.075 |
| Model control group | | 0.046 ± 0.014# | 0.176 ± 0.051# |
| Embodiment 9 | 1 | 0.064 ± 0.024 | 0.182 ± 0.042 |
| Embodiment 10 | 1 | 0.065 ± 0.023 | 0.180 ± 0.043 |
| Embodiment 11 | 1 | 0.080 ± 0.020 | 0.195 ± 0.048 |
| Embodiment 12 | 1 | 0.066 ± 0.022 | 0.183 ± 0.045 |
| Embodiment 13 | 1 | 0.062 ± 0.018 | 0.180 ± 0.046 |
| Embodiment 14 | 1 | 0.060 ± 0.019 | 0.179 ± 0.047 |
| Embodiment 15 | 1 | 0.082 ± 0.015 | 0.192 ± 0.050 |
| Embodiment 16 | 1 | 0.063 ± 0.023 | 0.178 ± 0.048 |

In Embodiment 9-12, only the weight ratio of the marine algal glycoprotein and glucuronic acid is changed. From the experimental results, Embodiment 11 is the most preferred embodiment;

In Embodiment 13-16, only the weight ratio of the marine algal glycoprotein, glucuronic acid and natural indigo is changed. From the experimental results, Embodiment 15 is the most preferred embodiment;

Embodiment 17 A Medicament for Use in Treating Diabetes

It comprises, by weight content, the following components:

1 portion of marine algal glycoprotein, 6 portions of natural indigo, 7 portions of amomum cardamomum, and 1 portion of glucuronic acid.

The said marine algal glycoprotein comprises, by weight content, 30% sugar and 50% protein.

The molecular weight is 50 kDa;

The said marine algae is blue algae;

The said sugar is a polysaccharide;

The said polysaccharide comprises: glucose, mannose, rhamnose, galactose;

The said protein comprises: aspartic acid, glutamic acid, glycine, arginine, lysine, serine, and threonine.

Embodiment 18 A Medicament for Use in Treating Diabetes

Like Embodiment 17, only the ratio of marine algal glycoprotein, natural indigo, amomum cardamomum and glucuronic acid is changed as follows:

It comprises, by weight content, the following components:

45 portions of marine algal glycoprotein, 9 portions of natural indigo, 13 portions of amomum cardamomum, and 8 portions of glucuronic acid.

Embodiment 19 A Medicament for Use in Treating Diabetes

Like Embodiment 17, only the ratio of marine algal glycoprotein, natural indigo, amomum cardamomum and glucuronic acid is changed as follows:

It comprises, by weight content, the following components:

99 portions of marine algal glycoprotein, 14 portions of natural indigo, 15 portions of amomum cardamomum, and 16 portion of glucuronic acid.

Embodiment 20 A Medicament for Use in Treating Diabetes

It comprises, by weight content, the following components:

1 portion of marine algal glycoprotein, 6 portions of natural indigo, 7 portions of amomum cardamomum, 8 portions of chrysanthemum and 8 portions of radix puerariae.

The said marine algal glycoprotein comprises, by weight content, 50% sugar and 20% protein.

The molecular weight is 200 kDa;

The said marine alga is blue alga;

The said sugar is a polysaccharide;

The said polysaccharide comprises: glucose, mannose, rhamnose, galactose;

The said protein comprises: aspartic acid, glutamic acid, glycine, arginine, lysine, serine, and threonine.

Embodiment 21 A Medicament for Use in Treating Diabetes

Like Embodiment 20, only the weight ratio of marine algal glycoprotein, natural indigo, amomum cardamomum, chrysanthemum and radix puerariae is changed as follows:

It comprises, by weight content, the following components:

60 portions of marine algal glycoprotein, 9 portions of natural indigo, 10 portions of amomum cardamomum, 11 portions of chrysanthemum and 9 portions of radix puerariae.

Embodiment 22 A Medicament for Use in Treating Diabetes

Like Embodiment 20, only the weight ratio of marine algal glycoprotein, natural indigo, amomum cardamomum, chrysanthemum and radix puerariae is changed as follows:

It comprises, by weight content, the following components:

99 portions of marine algal glycoprotein, 14 portions of natural indigo, 15 portions of amomum cardamomum, 12 portions of chrysanthemum and 10 portions of radix puerariae.

Application of the Said Medicament in Embodiment 17-Embodiment 22 in Treating Diabetes Using the test method said in Embodiment 7 and Embodiment 8, the medicament said in Embodiment 17-Embodiment 22 in this invention groups have the following application effects:

TABLE 7

The effect of the medicament hereof on blood glucose of a rat model of streptozotocin-induced diabetes

| Group | Dose (g/day) | Blood glucose before administration (mmol/L) | Blood glucose after administration at different times (mmol/L) | | | |
|---|---|---|---|---|---|---|
| | | | One Week | Two Weeks | Three Weeks | Four Weeks |
| Normal control group | — | 4.45 ± 0.71 | 4.33 ± 0.79 | 4.40 ± 0.63 | 5.30 ± 0.73 | 6.55 ± 0.68 |
| Model control group | — | 27.15 ± 6.09 | 29.33 ± 5.51 | 33.51 ± 6.27 | 35.79 ± 7.12 | 39.87 ± 5.96 |
| Embodiment 17 | 4 | 27.08 ± 5.95 | 19.23 ± 5.92 | 17.32 ± 7.49 | 15.01 ± 5.83 | 12.30 ± 9.13 |
| Embodiment 18 | 4 | 27.19 ± 5.82 | 19.28 ± 5.74 | 17.45 ± 7.25 | 15.45 ± 5.80 | 12.26 ± 8.71 |
| Embodiment 19 | 4 | 27.13 ± 5.72 | 16.35 ± 5.53 | 15.78 ± 7.58 | 12.36 ± 5.57 | 9.24 ± 8.60 |
| Embodiment 20 | 4 | 27.06 ± 5.91 | 19.28 ± 5.74 | 17.45 ± 7.05 | 15.45 ± 5.64 | 12.26 ± 8.70 |
| Embodiment 21 | 4 | 27.06 ± 5.91 | 19.28 ± 5.74 | 17.45 ± 7.37 | 15.45 ± 5.90 | 12.26 ± 8.61 |
| Embodiment 22 | 4 | 27.12 ± 6.35 | 19.28 ± 5.74 | 17.45 ± 7.45 | 15.45 ± 5.84 | 12.26 ± 8.51 |

TABLE 8

The effect of the medicament hereof on urine glucose

| | Embodiment 17 | Embodiment 18 | Embodiment 19 | Embodiment 20 | Embodiment 21 | Embodiment 22 |
|---|---|---|---|---|---|---|
| | Glucose in urine mmol/L | | | | | |
| 16-30 | 0.48 | 0 | 0.45 | 0.40 | 0 | 0.36 |
| 31-45 | 10.8 | 0 | 10.5 | 12.4 | 0 | 11.8 |
| 46-60 | 9.2 | 3.5 | 10.9 | 11.6 | 3.6 | 13.2 |
| 61-75 | 14.7 | 10 | 14.9 | 12.5 | 9.8 | 13.8 |

The medicament hereof has no adverse effect, and has a small fluctuation in blood glucose and urine glucose after being withdrawn for 2 months; for patients aged from 16 to 45 years old, the blood glucose concentration rises only by 1.2%, and the urine glucose is ≤0.5 mmol/L; for patients aged from 46 to 75 years old, the blood glucose concentration rises by 2.2%, and the urine glucose concentration rises by 5.0%.

TABLE 9

Effect of the medicament hereof on the immune organs of rat model induced by streptozotocin-induced diabetes

| Group | Dose (g/day) | Thymus (g/100 g Weight) | Spleen (g/100 g Weight) |
|---|---|---|---|
| Normal control group | | 0.092 ± 0.016 | 0.204 ± 0.075 |
| Model control group | | 0.046 ± 0.014# | 0.176 ± 0.051# |
| Embodiment 17 | 1 | 0.068 ± 0.024 | 0.182 ± 0.043 |
| Embodiment 18 | 1 | 0.093 ± 0.023 | 0.203 ± 0.042 |
| Embodiment 19 | 1 | 0.070 ± 0.020 | 0.183 ± 0.047 |
| Embodiment 20 | 1 | 0.071 ± 0.022 | 0.183 ± 0.046 |
| Embodiment 21 | 1 | 0.092 ± 0.018 | 0.202 ± 0.043 |
| Embodiment 22 | 1 | 0.068 ± 0.019 | 0.179 ± 0.047 |

In Embodiment 17-19, only the weight ratio of the marine algae glycoprotein, barley, white cardamom, and glucuronic acid was changed. From the experimental results, Embodiment 18 is the most preferred embodiment;

In Embodiments 20-22, only the weight ratio of the marine algae glycoprotein, barley, white cardamom, chrysanthemum and kudzuvine root is changed. From the experimental results, Embodiment 21 is the most preferred embodiment.

Embodiment 23 A Medicament for Use in Treating Diabetes

It comprises, by weight content, the following components:

70 portions of marine algal glycoprotein, 8 portions of poria cocos, 3 portions of herba dendrobii, 5 portions of valerian, 2 portions of pipewort, and 3 portions of gardenia.

The said marine algal glycoprotein comprises, by weight content, 8% sugar and 80% protein.

The molecular weight is 10 kDa;

The said marine algae is blue algae;

The said sugar, by weight, comprises the following components: 55 portions of glucose, 22 portions of mannose, 13 portions of rhamnose and 8 portions of galactose;

The protein mentioned, by weight, includes the following components: 13 portions of aspartic acid, 12 portions of glutamate and 8 portions of glycine.

Embodiment 24 A Medicament for Use in Treating Diabetes

It comprises, by weight content, the following components:

80 portions of marine algal glycoprotein, 3 portions of anemarrhena, 5 portions of broadleaf holly leaf, 4 portions of bitter melon, 6 portions of green tea leaves and 4 portions of folium eucommiae.

The said marine algal glycoprotein comprises, by weight content, 9% sugar and 78% protein.

The molecular weight is 14 kDa;

The said marine algae is blue algae;

The said sugar, by weight, comprises the following components: 55 portions of glucose, 22 portions of mannose, 13 portions of rhamnose and 8 portions of galactose;

The protein mentioned, by weight, includes the following components: 13 portions of aspartic acid, 12 portions of glutamate and 8 portions of glycine.

Embodiment 25 A Medicament for Use in Treating Diabetes

It comprises, by weight content, the following components:

86 portions of marine algal glycoprotein, 4 portions of fragrant solomonseal rhizome, 5 portions of fimbriatestipulate begonia herb, 8 portions of spinach root, 7 portions of lily, and 9 portions of paper mulberry fruit;

The said marine algal glycoprotein comprises, by weight content, 11% sugar and 75% protein.

The molecular weight is 17 kDa;

The said marine algae is blue algae;

The said sugar, by weight, comprises the following components: 55 portions of glucose, 22 portions of mannose, 13 portions of rhamnose and 8 portions of galactose;

The protein mentioned, by weight, includes the following components: 13 portions of aspartic acid, 12 portions of glutamate and 8 portions of glycine.

Embodiment 26 A Medicament for Use in Treating Diabetes

It comprises, by weight content, the following components:

80 portions of marine algal glycoprotein, 4 portions of astragalus root, 5 portions of purslane, 7 portions of mint, 8 portions of single-leaved chastetree fruit, and 9 portions of Japanese ginseng;

The said marine algal glycoprotein comprises, by weight content, 12% sugar and 70% protein.

The molecular weight is 18 kDa;

The marine algae is platymonas;

The said sugar, by weight, comprises the following components: 60 portions of glucose, 30 portions of mannose, 15 portions of rhamnose and 13 portions of galactose;

The protein mentioned, by weight, includes the following components: 17 portions of aspartic acid, 21 portions of glutamate and 13 portions of glycine.

Embodiment 27 Preparation Method of a Medicament for Use in Treating Diabetes Step 1: Weighing Weigh the marine algal glycoprotein and all Chinese medicine components according to the formula;

Step 2: Extraction of Chinese Medicine (1) Washing

Wash all Chinese medicine components with clear water, and remove the impurities;

(2) Crash and Microwave Extraction

The Chinese medicine is pulverized into 100-mesh medicinal material powder, 10 times of 50% ethanol is added, the temperature is controlled at 60° C., microwave radiation is performed at the microwave irradiation of 260 W, microwave wavelength of 130 mm, a frequency of 1200 MHz for 5 min, then filtration is carried out, and finally the filtrate is collected;

The medicine dregs are separated, 12 times of clear water is added, the temperature is controlled at 50° C., microwave radiation is performed at the microwave irradiation of 200 W, microwave wavelength of 1430 mm, a frequency of 1250 MHz for 5 min, then filtration is carried out, and finally the filtrate is collected;

Pool the filtrate collected from the two procedures; atomize and dry to prepare them into Chinese medicine powder;

After the aforementioned atomization and drying, pool the above filtrates collected from the two procedures; filter them through a 0.45 μm microporous membrane to obtain the subsequent filtrate, and the obtained subsequent filtrate is introduced into a dual-flow spiral nozzle of a Büchi290 small-sized spray dryer through a peristaltic pump, and the inlet temperature is controlled to 125° C., the feeding rate to 3 mL/min, and atomize and dry them.

Step 3 Add Marine Algae Glycoprotein

Evenly mix the marine algae glycoprotein powder and the said Chinese medicine powder; prepare them into the medicaments of different dosage forms such as capsules and tablets.

Application of the Said Medicament in Embodiment 23-Embodiment 26 in Treating Diabetes Using the test method said in Embodiment 7 and Embodiment 8, the medicament said in Embodiment 23-Embodiment 26 in this invention groups have the following application effects:

TABLE 10

The effect of the medicament hereof on blood glucose of a rat model of streptozotocin-induced diabetes

| Group | Dose (g/day) | Blood glucose before administration (mmol/L) | Blood glucose after administration at different times (mmol/L) | | | |
|---|---|---|---|---|---|---|
| | | | One Week | Two Weeks | Three Weeks | Four Weeks |
| Normal control group | — | 4.45 ± 0.71 | 4.33 ± 0.79 | 4.40 ± 0.63 | 5.30 ± 0.73 | 6.55 ± 0.68 |
| Model control group | — | 27.15 ± 6.09 | 29.33 ± 5.51 | 33.51 ± 6.27 | 35.79 ± 7.12 | 39.87 ± 5.96 |
| Embodiment 23 | 4 | 27.08 ± 5.95 | 17.23 ± 5.92 | 16.32 ± 7.49 | 13.01 ± 5.83 | 7.30 ± 9.13 |
| Embodiment 24 | 4 | 27.19 ± 5.82 | 17.00 ± 5.74 | 16.45 ± 7.25 | 13.36 ± 5.37 | 7.68 ± 8.60 |
| Embodiment 25 | 4 | 27.13 ± 5.72 | 17.35 ± 5.53 | 16.78 ± 7.58 | 12.36 ± 5.27 | 8.24 ± 8.60 |
| Embodiment 26 | 4 | 27.06 ± 5.91 | 17.26 ± 5.74 | 16.46 ± 7.05 | 13.45 ± 5.64 | 7.26 ± 8.70 |

TABLE 11

The effect of the medicament hereof on urine glucose

| | Embodiment 23 | Embodiment 24 | Embodiment 25 | Embodiment 26 |
|---|---|---|---|---|
| | | Glucose in urine mmol/L | | |
| 16-30 | 0.32 | 0.12 | 0.25 | 0.20 |
| 31-45 | 5.8 | 5.6 | 5.5 | 6.8 |
| 46-60 | 7.2 | 7.5 | 7.9 | 8.6 |
| 61-75 | 6.7 | 6.9 | 6.3 | 6.5 |

TABLE 12

Effect of the medicament hereof on the immune organs of rat model induced by streptozotocin-induced diabetes

| Group | Dose (g/day) | Thymus (g/100 g Weight) | Spleen (g/100 g Weight) |
|---|---|---|---|
| Normal control group | | 0.092 ± 0.016 | 0.204 ± 0.075 |
| Model control group | | 0.046 ± 0.014# | 0.176 ± 0.051# |
| Embodiment 23 | 1 | 0.088 ± 0.024 | 0.192 ± 0.043 |
| Embodiment 24 | 1 | 0.083 ± 0.023 | 0.200 ± 0.042 |
| Embodiment 25 | 1 | 0.078 ± 0.020 | 0.193 ± 0.047 |
| Embodiment 26 | 1 | 0.079 ± 0.022 | 0.189 ± 0.047 |

The medicaments thereof have a pH of between 5.3 and 9.8, preferably between 6.5 and 7.5.

The invention has been subjected to a large number of experiments, and we have carried out multiple tests using a mixture of marine shells, bones of livestock and poultry, a mixture of protides, polysaccharides and proteins extracted from the skeleton of marine animals, and the objectives of the invention have also been achieved.

Embodiment 28 A Medicament for Use in Treating Diabetes

The said medicament is a mixture of polysaccharides and proteins;

The said medicament comprises, by weight content, 1-99% polysaccharide and 1-99% protein.

The said polysaccharide comprises: glucose, mannose, rhamnose, galactose;

The said protein comprises: aspartic acid, glutamic acid, glycine, arginine, lysine, serine, and threonine.

As for the said mixture of polysaccharide and the protein, the polysaccharide has a molecular weight of 0.2-3000 kDa and the protein has a molecular weight of 0.2-3000 kDa.

The mixture of polysaccharides and proteins, further a mixture of algal polysaccharides and algal proteins;

A mixture of the algal polysaccharide and the algal protein also comprises a pigment;

The said pigment is a natural pigment contained in the algal substance;

The said algal protein may be phycocyanin, phycoerythrin or algae xanthoprotein.

The said glycoprotein includes synthetic glycoprotein, synthetic polysaccharide and protein.

The medicament hereof has a No Observed Adverse Effect Level (NOAEL) of 1.6 g/kg for 12-week oral administration for dogs, which is equivalent to 50 times the equivalent dose for humans, so it is concluded that the safety of the clinical trial can be guaranteed.

The medicine described in the invention can also be a health care product or a food.

The basic principles and main features of the present invention and the advantages of the present invention are shown and described above. It should be understood by the technicians in this field that, the present invention is not limited by the foregoing embodiments, and that what are described in the aforementioned embodiments and instructions are only the principles of this invention; without departing from the spirit and scope of the invention, this invention may be subject to various changes and modifications, which will be included within the scope of the invention as claimed. The scope of the invention is defined by the appended claims and their equivalents.

What is claimed is:

1. A medicament for use in treating diabetes, wherein the medicament comprises 1-99 portions of a glycoprotein, 4-16 portions of indigo naturalis, 7-15 portions of white cardomomum and 1-16 portions of glucuronic acid by weight, wherein the mount of glycoprotein is a therapeutically effective amount that treats diabetes.

2. The medicament of claim 1, wherein the glycoprotein is a marine algal glycoprotein.

3. The medicament of claim 2, wherein the marine algal glycoprotein comprises 1-99% sugar and 1-99% protein by weight.

4. The medicament of claim 2, wherein the marine algal glycoprotein has a molecular weight of 0.2 to 3000 kDa.

5. A medicament for use in treating diabetes, wherein the medicament comprises 1-99 portions of a glycoprotein, 1-20 portions of glucuronic acid and 3-10 portions of Indigo naturalis by weight, wherein the amount of the glycoprotein is a therapeutically effective amount that treats diabetes.

6. The medicament of claim 2, wherein the marine algal glycoprotein comes from a marine alga that is selected from the group consisting of a spirulina, a green alga, a red alga, a gold alga and a brown alga.

7. The medicament of claim 1, further comprising 8-12 portions of Chyrsanthemum and 8-10 portions of Radix puerariae by weight.

8. The medicament of claim 5, wherein the glycoprotein comprises 1-99% sugar and 1-99% protein by weight.

9. The medicament of claim 6, wherein the marine algal glycoprotein comprises 1-99% sugar and 1-99% protein by weight.

10. The medicament of claim 7, wherein the glycoprotein comprises 1-99% sugar and 1-99% protein by weight.

* * * * *